(12) United States Patent
Sato

(10) Patent No.: US 10,034,654 B2
(45) Date of Patent: Jul. 31, 2018

(54) ULTRASOUND UNIT AND ULTRASOUND ENDOSCOPE

(71) Applicant: OLYMPUS CORPORATION, Tokyo (JP)

(72) Inventor: Ken Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 449 days.

(21) Appl. No.: 14/565,952

(22) Filed: Dec. 10, 2014

(65) Prior Publication Data

US 2015/0087993 A1 Mar. 26, 2015

Related U.S. Application Data

(63) Continuation of application No. PCT/JP2013/063173, filed on May 10, 2013.

(30) Foreign Application Priority Data

Jun. 11, 2012 (JP) ................................. 2012-132026

(51) Int. Cl.
*A61B 8/00* (2006.01)
*H02N 1/08* (2006.01)
*A61B 8/12* (2006.01)
*A61B 1/005* (2006.01)
*B06B 1/02* (2006.01)

(52) U.S. Cl.
CPC ............ *A61B 8/4483* (2013.01); *A61B 1/005* (2013.01); *A61B 8/12* (2013.01); *A61B 8/445* (2013.01); *A61B 8/4494* (2013.01); *B06B 1/0292* (2013.01); *H02N 1/08* (2013.01); *A61B 8/4455* (2013.01); *B06B 2201/20* (2013.01)

(58) Field of Classification Search
CPC ........... A61B 1/005; A61B 8/12; A61B 8/445; A61B 8/4455; A61B 8/4483; A61B 8/4494; B06B 1/0292; B06B 2201/20; H02N 1/08
See application file for complete search history.

(56) References Cited

U.S. PATENT DOCUMENTS 6,314,057 B1 * 11/2001 Solomon ............... B06B 1/0292
367/174
2003/0028109 A1 2/2003 Miller

FOREIGN PATENT DOCUMENTS

EP   1 764 162 A1   7/2007
JP   03-165749 A    7/1991
(Continued)

OTHER PUBLICATIONS

Extended Supplementary European Search Report dated Feb. 1, 2016 from related European Application No. 13 80 4607.3.
(Continued)

*Primary Examiner* — Michael Rozanski
(74) *Attorney, Agent, or Firm* — Scully, Scott, Murphy & Presser, P.C.

(57) ABSTRACT

An ultrasound unit includes a plurality of elements each including N cells, in each of which a bottom electrode and a top electrode that constitutes a membrane are arranged facing each other with a cavity therebetween, wherein the element has $N_1$ first cells and $N_2$ (where $N_1 \neq N_2$, $N_1 + N_2 = N$) second cells having higher reception sensitivity and lower transmission sensitivity than the first cells.

5 Claims, 4 Drawing Sheets

(56) References Cited

FOREIGN PATENT DOCUMENTS

| | | | |
|---|---|---|---|
| JP | 2002-336248 | A | 11/2002 |
| JP | 2005-510264 | A | 4/2005 |
| JP | 2009-050560 | A | 3/2009 |
| JP | 2011-025055 | A | 2/2011 |
| JP | 2013-034665 | A | 2/2013 |
| WO | 2011/021358 | A2 | 2/2011 |

OTHER PUBLICATIONS

International Search Report dated Jul. 23, 2013 issued in PCT/JP2013/063173.

* cited by examiner

US 10,034,654 B2

ULTRASOUND UNIT AND ULTRASOUND ENDOSCOPE

CROSS REFERENCE TO RELATED APPLICATION

This application is a continuation application of PCT/JP2013/063173 filed on May 10, 2013 and claims benefit of Japanese Application No. 2012-132026 filed in Japan on Jun. 11, 2012, the entire contents of which are incorporated herein by this reference.

BACKGROUND OF THE INVENTION

1. Field of the Invention

The present invention relates to an ultrasound unit having a plurality of capacitive ultrasound transducer cells, and an ultrasound endoscope including the ultrasound unit.

2. Description of the Related Art

An ultrasound diagnostic method for performing diagnosis by applying ultrasound to a subject, and visualizing an internal state of a body from an echo signal has been popular. An ultrasound endoscope is one of ultrasound diagnostic apparatuses used for the ultrasound diagnostic method. In the ultrasound endoscope, an ultrasound unit is disposed at a distal end portion of an insertion section that is to be inserted into a body. The ultrasound unit has a function to convert an electrical signal to ultrasound and transmit the ultrasound into a body, and also to receive ultrasound reflected in the body and convert the ultrasound to an electrical signal.

In the ultrasound unit, a piezoelectric ultrasound transducer using a piezoelectric ceramic material (e.g., PZT: lead zirconate titanate), or a capacitive ultrasound transducer produced by using an MEMS technology (capacitive micromachined ultrasonic transducer: c-MUT) is used as an ultrasound transducer.

In a c-MUT type cell, a bottom electrode and a top electrode that constitutes a membrane are arranged facing each other with a cavity therebetween. When a voltage is applied between the electrodes of the cell, the membrane is deformed by an electrostatic force to generate ultrasound. On the other hand, when reflected ultrasound (echoes) reflected from an object enters the cell, the membrane is deformed. Thus, ultrasound is received by measuring capacitance between the electrodes.

Here, increasing transmission sensitivity and increasing reception sensitivity of the cell contradict. Therefore, for example, Japanese Patent Application Laid-Open Publication No. 2005-510264 discloses an ultrasound unit having a transmit-only cell having a structure emphasizing transmission sensitivity, and a receive-only cell having a structure emphasizing reception sensitivity.

SUMMARY OF THE INVENTION

An ultrasound unit of an embodiment of the present invention includes a plurality of ultrasound transducer elements each including N ultrasound transducer cells, in each of which a bottom electrode and a top electrode that constitutes a membrane are arranged facing each other with a cavity therebetween, wherein the ultrasound transducer element has $N_1$ first ultrasound transducer cells, and $N_2$ (where $N_1 \neq N_2$, $N_1 + N_2 = N$) second ultrasound transducer cells having higher reception sensitivity and lower transmission sensitivity than the first ultrasound transducer cells.

Also, an ultrasound endoscope of another embodiment of the present invention includes an ultrasound unit including a plurality of ultrasound transducer elements each including N ultrasound transducer cells, in each of which a bottom electrode and a top electrode that constitutes a membrane are arranged facing each other with a cavity therebetween, wherein the ultrasound transducer element has $N_1$ first ultrasound transducer cells, and $N_2$ (where $N_1 \neq N_2$, $N_1 + N_2 = N$) second ultrasound transducer cells having higher reception sensitivity and lower transmission sensitivity than the first ultrasound transducer cells.

DETAILED DESCRIPTION OF THE PREFERRED EMBODIMENT

First Embodiment

Hereinafter, an ultrasound unit 30 and an ultrasound endoscope 2 having the ultrasound unit 30 of a first embodiment are described by reference to the drawings. Note that all the drawings are schematic views for explanation, and the number of constituent elements, sizes thereof, and a ratio of the sizes etc. are different from actual values.

<Configuration of an Ultrasound Endoscope System>

Figure 1:
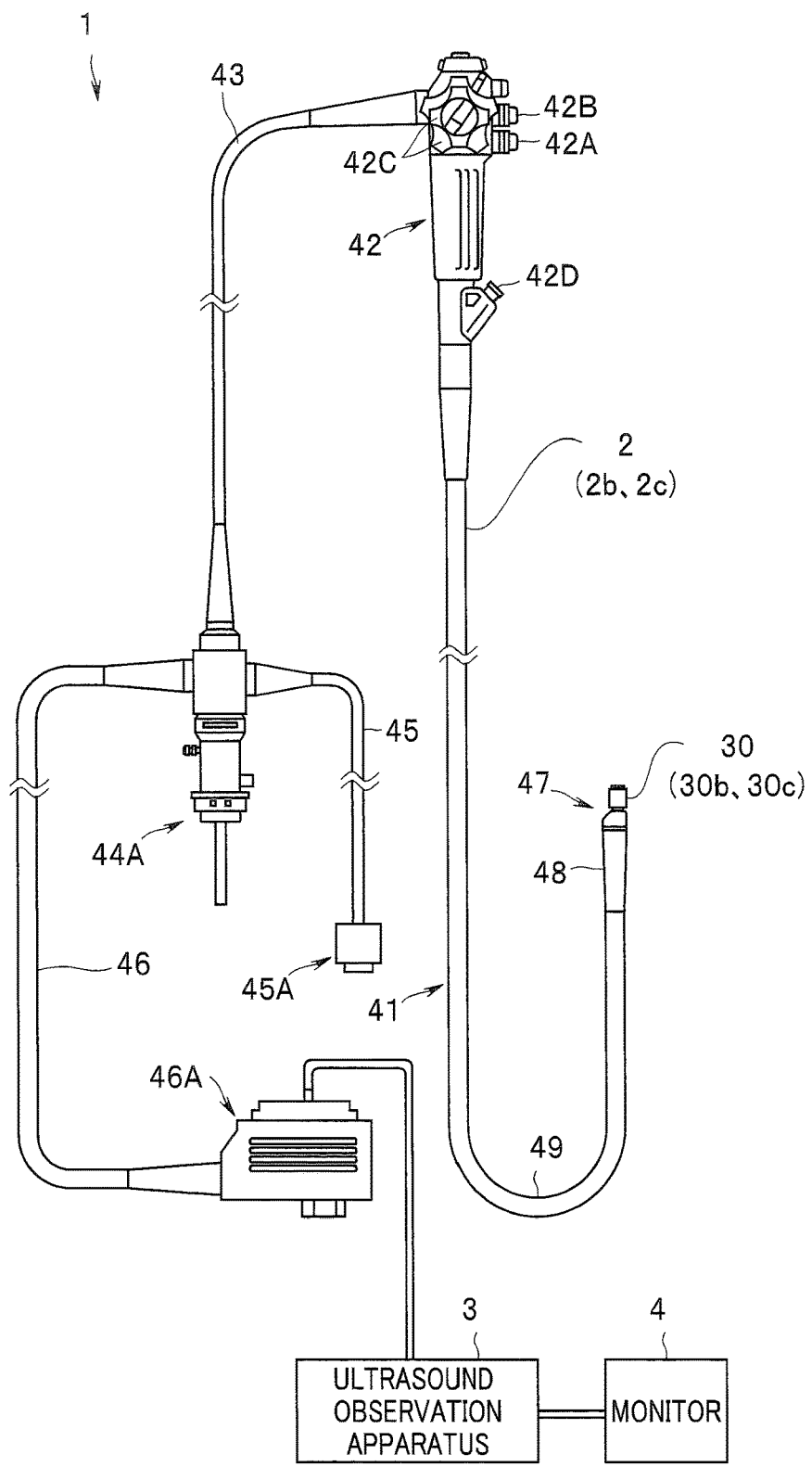
FIG. 1 is an exterior view for explaining an ultrasound endoscope of a first embodiment.

As shown in FIG. 1, the ultrasound endoscope 2 together with an ultrasound observation apparatus 3 and a monitor 4 constitute an ultrasound endoscope system 1. The ultrasound endoscope 2 includes an elongated insertion section 41 that is to be inserted into a body, an operation section 42 that is arranged at a proximal end of the insertion section 41, and a universal cord 43 that extends out from a side portion of the operation section 42.

A connector 44A that is connected to a light source apparatus (not shown) is disposed at a proximal end portion of the universal cord 43. A cable 45 that is detachably connected to a camera control unit (not shown) via a connector 45A, and a cable 46 that is detachably connected to the ultrasound observation apparatus 3 via a connector 46A extend out from the connector 44A. The monitor 4 is connected to the ultrasound observation apparatus 3.

The insertion section 41 is configured by continuously providing a distal end portion 47, a bending portion 48 that is located at a rear end of the distal end portion 47, and a small-diameter and long flexible tube portion 49 having flexibility that is located at a rear end of the bending portion 48 and leads to the operation section 42, sequentially from a distal end side. The ultrasound unit 30 is disposed at the distal end portion 47 (see FIG. 2).

In the operation section 42, an angle knob 42A that performs bending control of the bending portion 48 in a desired direction, an air/water feeding button 42B that performs air feeding and water feeding operations, a suction button 42C that performs a suction operation, a treatment instrument insertion port 42D that serves as an inlet for a treatment instrument having a puncture needle or the like to be introduced into a body as described below, or the like are disposed.

Figure 2:
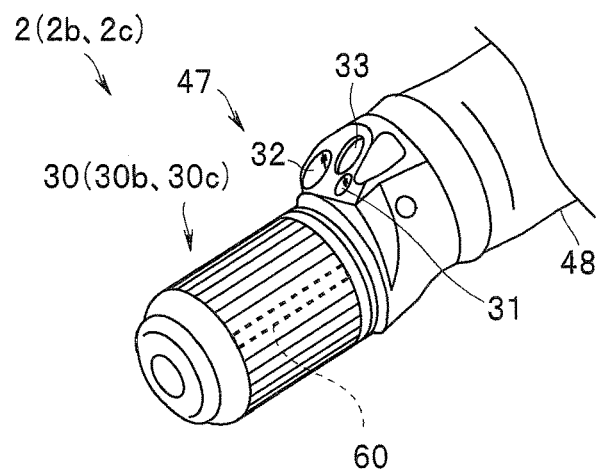
FIG. 2 is a perspective view for explaining a configuration of a distal end portion of the ultrasound endoscope of the first embodiment.

As shown in FIG. 2, an illumination lens cover 31 that constitutes an illumination optical system, an observation lens cover 32 of an observation optical system; a forceps port 33, and an unillustrated air/water feeding nozzle are disposed at the distal end portion 47 of the ultrasound endoscope 2 where the ultrasound unit 30 is disposed. As described below, the ultrasound unit 30 has a plurality of ultrasound transducer elements (hereinafter referred to as an "element") 60.

Figure 3:
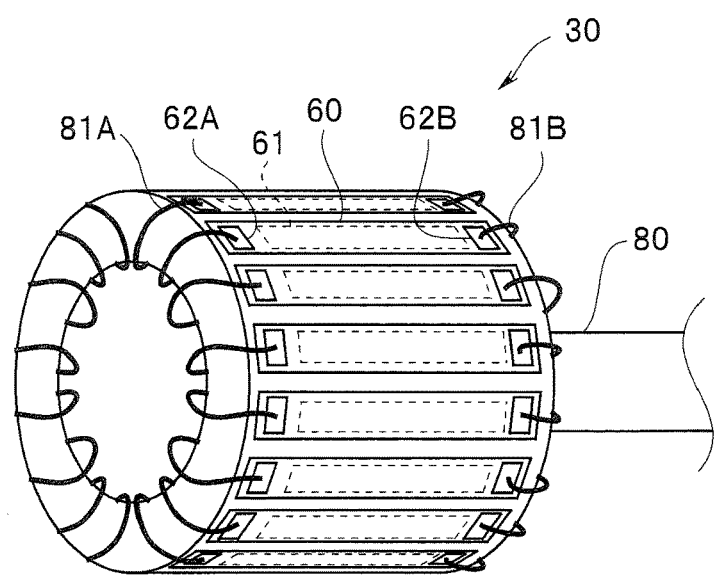
FIG. 3 is a perspective view for explaining an ultrasound unit of the first embodiment.

As shown in FIG. 3, an external electrode 62A is connected to a conducting wire 81A of a cable 80, and an external electrode 62B is connected to a conducting wire 81B of the cable 80.

Figure 4:
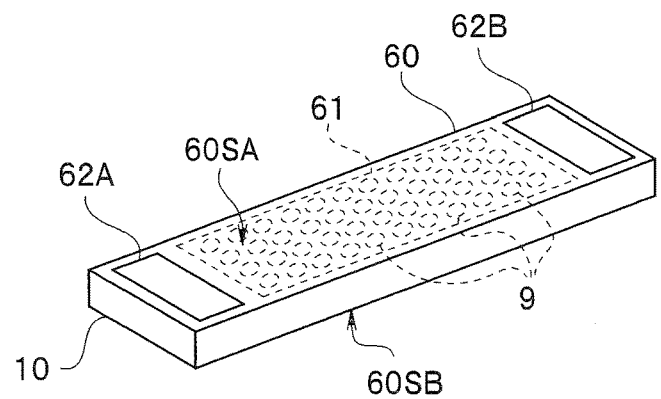
FIG. 4 is a perspective view for explaining an ultrasound transducer element of the ultrasound unit of the first embodiment.

As shown in FIG. 4, the element 60 that is a base unit for transmitting/receiving ultrasound has a first main face 60SA, and a second main face 60SB that faces the first main face 60SA. A transmitting/receiving section 61 that transmits/receives ultrasound is formed in a substantially center portion of the first main face 60SA of the element 60. The external electrodes 62A and 62B are disposed at both end portions of the first main face 60SA. As described below, the element 60 has a plurality of ultrasound transducer cells (hereinafter referred to as a "cell") 9.

Figure 5:
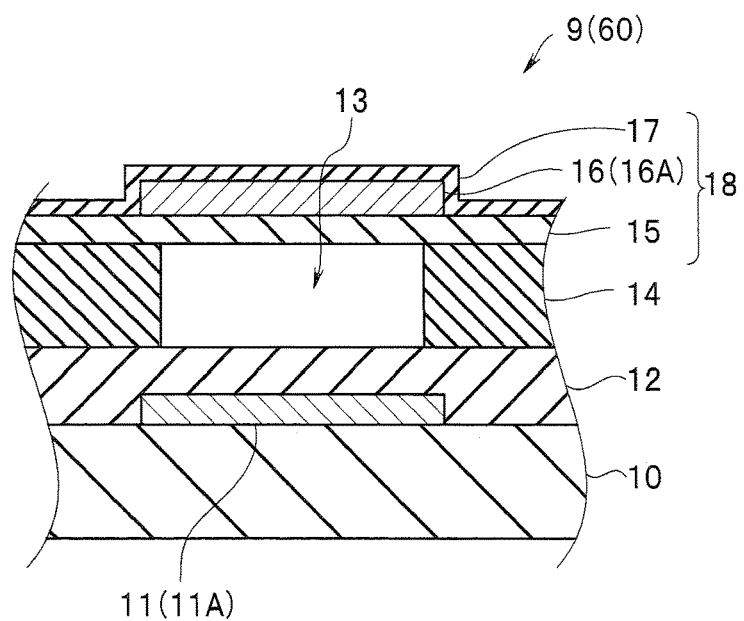
FIG. 5 is a sectional view for explaining a structure of an ultrasound transducer cell of the ultrasound unit of the first embodiment.

As shown in FIG. 5, the cell 9 of the element 60 has a bottom electrode layer 11, a bottom insulating layer 12, a cavity 13, a support layer 14 thereof, a top insulating layer 15, a top electrode layer 16, and a protective layer 17, which are sequentially laminated on a silicon substrate 10 that serves as a base. Note that dozens to thousands of cells 9 generally constitute one element 60 although FIG. 5 shows a sectional structure of one cell 9.

The bottom electrode layer 11 has a plurality of bottom electrodes 11A, and a plurality of bottom electrode interconnections (not shown) that extend from edge portions of the bottom electrodes 11A. The bottom electrode layer 11 is connected to the bottom electrodes 11A of another cell 9 of the same element 60. The top electrode layer 16 has a plurality of top electrodes 16A, and a plurality of top electrode interconnections (not shown) that extend from the top electrodes 16A. The top electrode layer 16 is connected to the top electrodes 16A of another cell 9 of the same element 60. Each of the cells 9 has the bottom electrodes 11A and the top electrodes 16A that are arranged facing each other with the cavity 13 therebetween.

As described above, all of the bottom electrodes 11A of the plurality of cells 9 arranged in the same element 60 are connected to each other, and all of the top electrodes 16A are also connected to each other. A drive voltage is applied to the bottom electrode layer 11, and the top electrode layer 16 is at ground potential.

When a pulse voltage is applied between the bottom electrode layer 11 and the top electrode layer 16 of the element 60, a membrane (vibration section) 18 including the top electrodes 16A is vibrated by an electrostatic force to generate ultrasound. Also, when ultrasound enters from outside, the membrane 18 is deformed to change an interval between the bottom electrode layer 11 and the top electrode layer 16. Thus, the ultrasound is converted to an electrical signal based on a change in capacitance.

Figure 6:
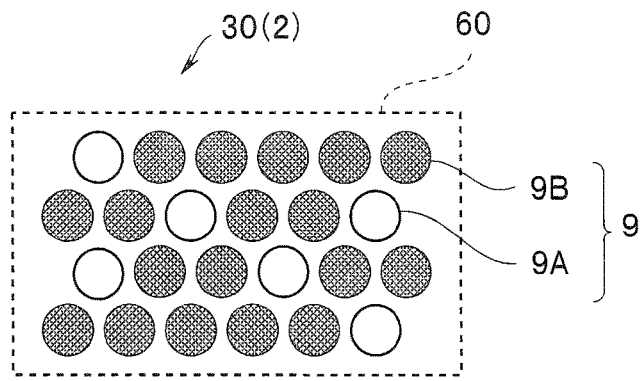
FIG. 6 is a top view for explaining arrangement or the like of the ultrasound transducer cells of the element of the ultrasound unit of the first embodiment.

As shown in FIG. 6, in the ultrasound unit 30, the N cells 9 of the element 60 include $N_{1a}$ first cells 9A and $N_{2a}$ second cells 9B (where $N_{1a} = N_{2a}$). The second cells 9B have higher reception sensitivity and lower transmission sensitivity than the first cells 9A. That is, the first cells 9A have transmission sensitivity $S_{T1a}$ and reception sensitivity $S_{R1a}$, and the second cells 9B have transmission sensitivity $S_{T2a}$ (where $S_{T1a} > S_{T2a}$), and reception sensitivity $S_{R2a}$ (where $S_{R1a} < S_{R2a}$). The transmission sensitivity and the reception sensitivity of the cells 9 can be optimized for transmission or reception by, for example, changing a thickness of the membrane 18.

Hereinafter, transmission/reception sensitivity S of the ultrasound unit 30 (the element 60) is defined as a product of transmission sensitivity $S_T$ (unit: Pa/V) and reception sensitivity $S_R$ (unit: V/Pa), and a condition under which maximum transmission/reception sensitivity S is obtained is theoretically derived.

A total number $N_a$ of the cells 9 of the element 60, a number $N_{1a}$ of the cells 9A, and a number $N_{2a}$ of the cells 9B are shown in following (Equation 11).

$$N_a = N_{1a} + N_{2a} \qquad \text{(Equation 11)}$$

Transmission sensitivity $S_{Ta}$ of the element 60 is shown in (Equation 12).

$$S_{Ta} = S_{T1a} \cdot N_{1a} + S_{T2a} \cdot N_{2a} = S_{T1a} \cdot N_{1a} + S_{T2a} \cdot (N_a - N_{1a}) \qquad \text{(Equation 12)}$$

On the other hand, reception sensitivity $S_{Ra}$ of the element 60 is shown in (Equation 13).

$$S_{Ra} = S_{R1a} \cdot N_{1a} + S_{R2a} \cdot N_{2a} = S_{R2a} \cdot N_{1a} + S_{R2a} \cdot (N_a - N_{1a}) \qquad \text{(Equation 13)}$$

That is, in the ultrasound unit 30 (the element 60), the first cells 9A having high transmission sensitivity and low reception sensitivity, and the second cells 9B having low transmission sensitivity and high reception sensitivity are both used for transmission and reception.

As already described above, transmission/reception sensitivity $S_a$ of the element 60 is defined in (Equation 14).

$$
\begin{aligned}
S_a &= S_{Ta} \cdot S_{Ra} \\
&= \{S_{T1a} \cdot N_1 + S_{T2a} \cdot (N_a - N_{1a})\} \\
&\quad \{S_{R1a} \cdot N_{1a} + S_{R2a} \cdot (N_a - N_{1a})\} \\
&= (S_{T1a} S_{R1a} + S_{T2a} S_{R2a} - S_{T1a} S_{R2a} - S_{T2a} S_{R1a}) \cdot \\
&\quad N_{1a}^2 + (S_{T1a} S_{R2a} + S_{T2a} S_{R1a} - 2 S_{T2a} S_{R2a}) \cdot \\
&\quad N_a N_{1a} + S_{T2a} S_{R2a} N_a^2 \\
&= (S_{T1a} - S_{T2a})(S_{R1a} - S_{R2a}) \\
&\quad \left\{ N_{1a} + \frac{S_{T1a} S_{R2a} + S_{T2a} S_{R1a} - 2 S_{T2a} S_{R2a}}{2(S_{T1a} - S_{T2a})(S_{R1a} - S_{R2a})} N_a \right\}^2 + \\
&\quad S_{T2a} S_{R2a} N_a^2 - \frac{(S_{T1a} S_{R2a} + S_{T2a} S_{R1a} - 2 S_{T2a} S_{R2a})^2 \cdot N_a^2}{4(S_{T1a} - S_{T2a})(S_{R1a} - S_{R2a})}
\end{aligned}
$$

(Equation 14)

The number $N_{1a}$ of the first cells 9A where maximum transmission/reception sensitivity $S_a$ is obtained is shown in (Equation 15) based on (Equation 14).

$$N_{1a} = \frac{2 S_{T2a} S_{R2a} - S_{T1a} S_{R2a} - S_{T2a} S_{R1a}}{2(S_{T1a} - S_{T2a})(S_{R1a} - S_{R2a})} N_a \qquad \text{(Equation 15)}$$

Note that the number $N_{2a}$ of the second cells 9B where the maximum transmission/reception sensitivity $S_a$ is obtained is shown in (Equation 16).

$$N_{2a} = N_a - N_{1a} \quad \text{(Equation 16)}$$
$$= \frac{2S_{T1a}S_{R1a} - S_{T1a}S_{R2a} - S_{T2a}S_{R1a}}{2(S_{T1a} - S_{T2a})(S_{R1a} - S_{R2a})} N_a$$

That is, the element 60 where the number $N_{1a}$ of the first cells 9A is configured as shown in (Equation 15) and the number $N_{2a}$ of the second cells 9B is configured as shown in (Equation 16) has the maximum transmission/reception sensitivity $S_a$.

As described above, the ultrasound unit 30 performs transmission and reception by using both the first cells 9A suitable for transmission and the second cells 9B suitable for reception. Therefore, the ultrasound unit 30 has higher transmission sensitivity than a conventional ultrasound unit that performs transmission by using only the first cells 9A suitable for transmission. Similarly, the ultrasound unit 30 has higher reception sensitivity than a conventional ultrasound unit that performs reception by using only the second cells 9B suitable for reception.

Furthermore, the ultrasound unit 30 having the first cells 9A in the number shown in (Equation 15) and the second cells 9B in the number shown in (Equation 16) has high transmission/reception sensitivity. The ultrasound endoscope 2 including the ultrasound unit 30 has high transmission/reception sensitivity.

Note that the number (a ratio) of the cells 9 is not strictly limited to the number shown in (Equation 15) or the like, and the number only needs to be within a range of ±10% from the number shown in (Equation 15) or the like according to a relationship of arrangement or the like within the element.

That is, the number $N_{1a}$ of the first cells 9A only needs to satisfy following (Expression 15A) with respect to the number (X) shown in (Equation 15).

$$0.91X \leq N_{1a} \leq 1.1X \quad \text{(Expression 15A)}$$

Hereinafter, a case of $S_{T2a} = \frac{1}{2}S_{T1a}$ and $S_{R2a} = 3S_{R1a}$ is described as a specific example.

The number $N_{1a}$ of the first cells 9A and the number $N_{2a}$ of the second cells 9B are given by (Equation 17) and (Equation 18) based on (Equation 15) and (Equation 16).

$$N_{1a} = \frac{2 \cdot 1/2 S_{T1a} \cdot 3S_{R1a} - S_{T1a} \cdot 3S_{R1a} - 1/2 S_{T2a} S_{R1a}}{2(S_{T1a} - 1/2 S_{T1a})(S_{R1a} - S_{R1a})} N_a \quad \text{(Equation 17)}$$
$$= \frac{-1/2 S_{T2a} S_{R1a}}{2(1/2 S_{T1a})(-2S_{R1a})} N_a$$
$$= \frac{-1/2 S_{T2a} S_{R1a}}{-2S_{T1a} S_{R1a}} \cdot N_a$$
$$= \frac{1}{4} N_a$$

$$N_{2a} = \frac{2S_{T1a}S_{R1a} - S_{T1a} \cdot 3S_{R1a} - 1/2 S_{T1a} S_{R1a}}{2(S_{T1a} - 1/2 S_{T1a})(S_{R1a} - 3S_{R1a})} N_a \quad \text{(Equation 18)}$$
$$= \frac{-3/2 S_{T1a} S_{R1a}}{-2S_{T1a} S_{R1a}} N_a$$
$$= \frac{3}{4} N_a$$

That is, by setting the number of the plurality of cells 9 of the element 60 such that the first cells 9A account for 25%, and the second cells 9B account for 75%, the maximum transmission/reception efficiency is obtained.

Note that the effect is obtained when the number $N_{1a}$ of the first cells 9A is 22.5% (25×0.9) or more to 27.5% (25×1.1) or less of the number $N_a$ of the plurality of cells 9 as already described above.

Second Embodiment

Next, an ultrasound unit 30b and an ultrasound endoscope 2b of a second embodiment are described. Since the ultrasound unit 30b and the like are similar to the ultrasound unit 30 and the like, the same constituent elements are assigned the same reference numerals, and description is omitted.

In an element 60b of the ultrasound unit 30b, first cells 9Ab in a number $N_{1b}$ are transmit-only cells each having an occupancy area $A_{1b}$, and second cells 9Bb in a number $N_{2b}$ are receive-only cells each having an occupancy area $A_{2b}$ (where $A_{1b} \neq A_{2b}$).

That is, in the ultrasound unit 30b, a bottom electrode of the first cell 9Ab and a bottom electrode of the second cell 9Bb, which are drive potential electrodes arranged in the element 60b, are not connected together. Note that a top electrode of the first cell 9Ab and a top electrode of the second cell 9Bb, which are ground potential electrodes, may be connected together.

When an area of the transmitting/receiving section 61 where the first cells 9Ab and the second cells 9Bb are arranged in the element 60b is A, and a total of the number of the ultrasound cells constituting the element 60b is $N_b$, a relationship of (Equation 21) and (Equation 22) holds.

$$N_b = N_{1b} + N_{2b} \quad \text{(Equation 21)}$$

$$A = A_{1b} \cdot N_{1b} + A_{2b} \cdot N_{2b} \quad \text{(Equation 22)}$$

Figure 7:
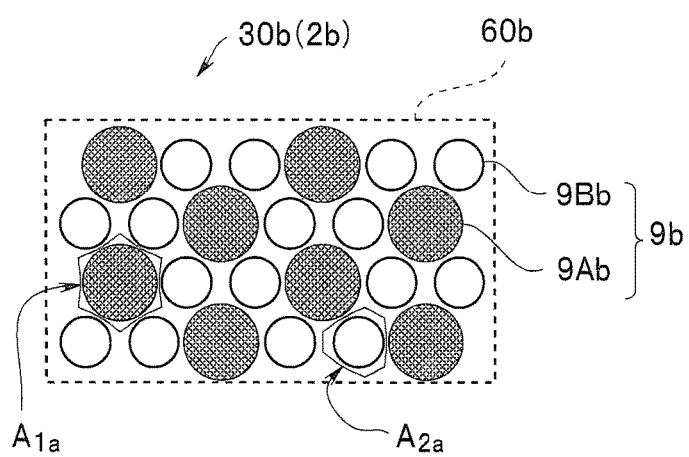
FIG. 7 is a top view for explaining arrangement or the like of ultrasound transducer cells of an element of an ultrasound unit of a second embodiment.

That is, the occupancy area of a cell 9b does not mean, for example; a diameter of each cavity, but is an area of a portion enclosed by a line connecting intermediate points between a center when the cell 9b is arranged in the element 60, and a center of another cell 9b around the cell 9b as shown in FIG. 7.

(Equation 23) is obtained by transforming (Equation 22).

$$N_{2b} = \frac{1}{A_{2b}}(A - A_{1b} \cdot N_{1b}) \quad \text{(Equation 23)}$$

When transmission sensitivity of the first cells 9Ab is $S_{Tb}$ and reception sensitivity of the second cells 9Bb is $S_{Rb}$, transmission/reception sensitivity $S_b$ of the element 60b is shown in (Equation 24).

$$S_b = (S_{Tb} \cdot N_{1b}) \cdot (S_{Rb} \cdot N_{2b}) \quad \text{(Equation 24)}$$
$$= S_{Tb}S_{Rb} \cdot \frac{1}{A_{2b}}\{(A - A_{1b} \cdot N_{1b})N_{1b}\}$$
$$= -S_{Tb}S_{Rb} \cdot \frac{A_{1b}}{A_{2b}}\left(N_{1b}^2 - \frac{A}{A_{1b}}N_{1b}\right)$$
$$= -S_{Tb}S_{Rb} \cdot \frac{A_{1b}}{A_{2b}}\left\{\left(N_{1b} - \frac{A}{2A_{1b}}\right)^2 - \left(\frac{A}{2A_{1b}}\right)^2\right\}$$

It is obvious from (Equation 24) that maximum transmission/reception sensitivity $S_b$ is obtained when the number $N_{1b}$ of the first cells 9Ab satisfies (Equation 25).

$$N_{1b} = \frac{A}{2A_{1b}} \quad \text{(Equation 25)}$$

Note that the number $N_{2b}$ of the second cells 9Bb in the above case is shown in (Equation 26).

$$N_{2b} = \frac{1}{A_{2b}}\left(A - A_{1b} \cdot \frac{A}{2A_{1b}}\right) = \frac{1}{A_{2b}}\left(A - \frac{A}{2}\right) = \frac{A}{2A_{2b}} \quad \text{(Equation 26)}$$

Therefore, (Equation 27) is obtained from a ratio of the numbers of the ultrasound cells 9Ab and 9Bb.

$$N_{1b} : N_{2b} = \frac{A}{2A_{1b}} : \frac{A}{2A_{2b}} \quad \text{(Equation 27)}$$

$$\frac{N_{2b}}{A_{1b}} = \frac{N_{1b}}{A_{2b}}$$

$$N_{2b} = \frac{A_{1b}}{A_{2b}} N_{1b}$$

A relationship of the numbers of the ultrasound cells 9Ab and 9Bb is obtained as in (Equation 28) based on (Equation 22) and (Equation 27).

$$N_b = N_{1b} + N_{2b} = \quad \text{(Equation 28)}$$

$$N_{1b} + \frac{A_{1b}}{A_{2b}} N_{1b} = \left(1 + \frac{A_{1b}}{A_{2b}}\right) N_{1b} = \frac{A_{1b} + A_{2b}}{A_{2b}} N_{1b}$$

Accordingly, the maximum transmission/reception sensitivity $S_b$ is obtained in the ultrasound unit 30b when (Equation 29) is satisfied.

$$N_{1b} = \frac{A_{2b}}{A_{1b} + A_{2b}} N_b \quad \text{(Equation 29)}$$

Note that the number $N_{2b}$ of the second cells 9Bb where the maximum transmission/reception sensitivity $S_b$ is obtained is shown in (Equation 30).

$$N_{2b} = \frac{A_{1b}}{A_{1b} + A_{2b}} N_b \quad \text{(Equation 30)}$$

Also, the number (the ratio) of the cells 9 is not strictly limited to the number shown in (Equation 29) or the like, and the number only needs to be within a range of ±10% from the number shown in (Equation 29) or the like according to a relationship of arrangement or the like within the element.

That is, the number $N_{1b}$ of the first cells 9Ab only needs to satisfy following (Expression 29A) with respect to the number (Y) shown in (Equation 29).

$$0.9Y \leq N_{1b} \leq 1.1Y \quad \text{(Expression 29A)}$$

Hereinafter, a case in which the area $A_{2b}$ of the second cell 9Bb is twice the area $A_{1b}$ of the first cell 9Ab, namely, $A_{2b} = 2A_{1b}$ is described as a specific example. The number $N_{1b}$ of the first cells 9Ab and the number $N_{2b}$ of the second cells 9Bb where the maximum transmission/reception sensitivity $S_b$ is obtained are shown in (Equation 31) and (Equation 32) based on (Equation 29) and (Equation 30).

$$N_{1b} = \frac{A_{2b}}{A_{1b} + A_{2b}} N_b = \frac{2A_{1b}}{A_{1b} + 2A_{1b}} N_b = \frac{2}{3} N_b \quad \text{(Equation 31)}$$

$$N_{2b} = \frac{A_{1b}}{A_{1b} + A_{2b}} N_b = \frac{A_{1b}}{A_{1b} + 2A_{1b}} N_b = \frac{1}{3} N_b \quad \text{(Equation 32)}$$

That is, by setting the number or the plurality of cells 9b of the element 60b such that the first cells 9Ab account for ⅔ of the number of cells, and the second cells 9Bb account for ⅓ of the number of cells, the maximum transmission/reception efficiency is obtained.

Note that the effect is obtained when the number $N_{1b}$ of the first cells 9Ab is 60% ((⅔)×0.9) or more to 73.3% ((⅔)×1.1) or less of the number $N_b$ of the plurality of cells 9 as already described above.

As described above, the ultrasound unit 30b performs transmission by using only the transmit-only first cells 9Ab, and performs reception by using only the receive-only second cells 9Bb. However, the occupancy area $A_{1b}$ of the first cell 9Ab and the occupancy area $A_{1b}$ of the second cell 9Bb differ from each other unlike in the conventional ultrasound unit.

As described above, in the element 60b having the transmit-only cells and the receive-only cells, the number (the ratio) of the cells where the transmission/reception sensitivity has a maximum value is not related to the transmission sensitivity or the reception sensitivity.

The ultrasound unit 30b where each of the elements 60b has the cells 9Ab and 9Bb in the numbers shown in (Equation 31) and (Equation 32) has high transmission/reception sensitivity. The ultrasound endoscope 2b including the ultrasound unit 30b has high transmission/reception sensitivity.

Third Embodiment

Figure 8:
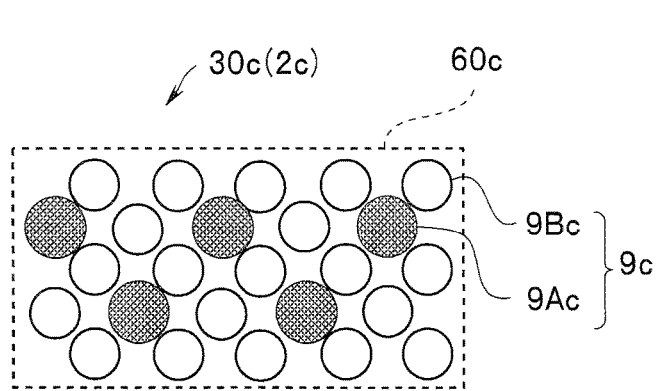
FIG. 8 is a top view for explaining arrangement or the like of ultrasound transducer cells of an element of an ultrasound unit of a third embodiment.

Next, an ultrasound unit 30c and an ultrasound endoscope 2c of a third embodiment are described with reference to FIG. 8. Since the ultrasound unit 30c and the like are similar to the ultrasound unit 30 and the like, the same constituent elements are assigned the same reference numerals, and description is omitted.

In an element 60c of the ultrasound unit 30c, an area where ultrasound cells can be arranged is $A_c$, first cells 9Ac has transmission sensitivity $S_{T1c}$, reception sensitivity $S_{R1c}$, and an area $A_{1c}$, and second cells 9Bc has transmission sensitivity $S_{T2c}$ (where $S_{T1c} > S_{T2c}$), reception sensitivity $S_{R2c}$ (where $S_{R1c} < S_{R2c}$), and an area $A_{2c}$ (where $A_{1c} \neq A_{2c}$).

That is, (Equation 41) holds.

$$A_c = A_{1c} \cdot N_{1c} + A_{2c} \cdot N_{2c} \quad \text{(Equation 41)}$$

(Equation 42) is obtained by transforming (Equation 41).

$$N_{2c} = \frac{1}{A_{2c}}(A_c - A_{1c} \cdot N_{1c}) \quad \text{(Equation 42)}$$

Transmission sensitivity $S_{Tc}$ of the element 60c is shown in (Equation 43).

$$S_{Tc} = S_{T1c} \cdot N_{1c} + S_{T2c} \cdot N_{2c} \quad \text{(Equation 43)}$$

On the other hand, reception sensitivity $S_{Rc}$ of the element $60c$ is shown in (Equation 44).

$$S_{Rc} = S_{R1c} \cdot N_{1c} + S_{R2} \cdot N_{2c} \quad \text{(Equation 44)}$$

Transmission/reception sensitivity $S_c$ of the element $60c$ is shown in (Equation 45).

$$\begin{aligned}
S_c &= S_{Tc} \cdot S_{Rc} \quad \text{(Equation 45)} \\
&= (S_{T1c} \cdot N_{1c} + S_{T2c} \cdot N_{2c})(S_{R1c} \cdot N_{1c} + S_{R2c} \cdot N_{2c}) \\
&= S_{T1c} S_{R1c} \cdot N_{1c}^2 + (S_{T1c} S_{R2c} + S_{T2c} S_{R1c}) N_{1c} N_{2c} + \\
&\quad S_{T2c} S_{R2c} \cdot N_{2c}^2 \\
&= S_{T1c} S_{R1c} \cdot N_{1c}^2 + \frac{1}{A_{2c}} (S_{T1c} S_{R2c} + S_{T2c} S_{R1c}) \\
&\quad (A_c - A_{1c} N_{1c}) N_{1c} + \frac{1}{A_{2c}^2} S_{T2c} S_{R2c} (A_c - A_{1c} N_{1c})^2
\end{aligned}$$

Here, α, γ, and γ are defined as follows.

$$\alpha = S_{T1c} S_{R1c} A_{2c}^2 - (S_{T1c} S_{R2c} + S_{T2c} S_{R1c}) A_{1c} A_{2c} + S_{T2c} S_{R2c} A_{1c}^2$$

$$\beta = \{(S_{T1c} S_{R2c} + S_{T2c} S_{R1c}) A_{2c} - 2 S_{T2c} S_{R2c} A_{1c}\} A_c$$

$$\gamma = S_{T2c} S_{R2c} A_c^2$$

Accordingly, the transmission/reception sensitivity $S_c$ is expressed in (Equation 46).

$$\begin{aligned}
S_c &= \frac{1}{A_{2c}^2}(\alpha N_{1c}^2 + \beta N_{1c} + \gamma) \quad \text{(Equation 46)} \\
&= \frac{1}{\alpha A_{2c}^2}\left\{\left(N_{1c} + \frac{\beta}{2\alpha}\right)^2 - \left(\frac{\beta}{2\alpha}\right)^2 + \frac{\gamma}{\alpha}\right\}
\end{aligned}$$

It is obvious from (Equation 46) that maximum transmission/reception sensitivity $S_c$ is obtained when a number $N_{1c}$ of the first cells 9Ac satisfies (Equation 47).

$$\begin{aligned}
N_{1c} &= -\frac{\beta}{2\alpha} \quad \text{(Equation 47)} \\
&= \frac{A_c}{2} \cdot \frac{2 S_{T2c} S_{R2c} A_{1c} - (S_{T1c} S_{R2c} + S_{T2c} S_{R1c}) A_{2c}}{S_{T1c} S_{R1c} A_{2c}^2 - (S_{T1c} S_{R2c} + S_{T2c} S_{R1c}) A_{1c} A_{2c} + S_{T2c} S_{R2c} A_{1c}^2}
\end{aligned}$$

On the other hand, a number $N_{2c}$ of the second cells 9Bc where the maximum transmission/reception sensitivity $S_c$ is obtained is shown in (Equation 48).

$$\begin{aligned}
N_{2c} &= \frac{1}{A_{2c}}(A_c - A_{1c} \cdot N_{1c}) \quad \text{(Equation 48)} \\
&= \frac{1}{A_{2c}}\left[A_c - A_{1c}\left\{\frac{A_c}{2} \cdot \frac{2 S_{T2c} S_{R2c} A_{1c} - (S_{T1c} S_{R2c} + S_{T2c} S_{R1c}) A_{2c}}{S_{T1c} S_{R1c} A_{2c}^2 - (S_{T1c} S_{R2c} + S_{T2c} S_{R1c}) A_{1c} A_{2c} + S_{T2c} S_{R2c} A_{1c}^2}\right\}\right] \\
&= \frac{A_c}{2} \cdot \frac{2 S_{T1c} S_{R1c} A_{2c} - (S_{T1c} S_{R2c} + S_{T2c} S_{R1c}) A_{1c}}{S_{T1c} S_{R1c} A_{2c}^2 - (S_{T1c} S_{R2c} + S_{T2c} S_{R1c}) A_{1c} A_{2c} + S_{T2c} S_{R2c} A_{1c}^2}
\end{aligned}$$

Therefore, (Equation 49) is obtained based on a ratio of the respective cell numbers.

$$N_{1c} : N_{2c} = 2 S_{T2c} S_{R2c} A_{1c} - (S_{T1c} S_{R2c} + S_{T2c} S_{R1c}) A_{2c} : 2 S_{T1c} S_{R1c} A_{2c} - (S_{T1c} S_{R2c} + S_{T2c} S_{R1c}) A_{1c} \quad \text{(Equation 49)}$$

$$N_{2c} = \frac{2 S_{T1c} S_{R1c} A_{2c} - (A_{T1c} S_{R2c} + S_{T2c} S_{R1c}) A_{1c}}{2 S_{T2c} S_{R2c} A_{1c} - (A_{T1c} S_{R2c} + S_{T2c} S_{R1c}) A_{2c}} N_{1c}$$

When a total of the number of the cells constituting the element $60c$ is $N_c$, (Equation 50) and (Equation 51) hold.

$$N_c = N_{1c} + N_{2c} \quad \text{(Equation 50)}$$

$$N_c = N_{1c} + \frac{2 S_{T1c} S_{R1c} A_{2c} - (S_{T1c} S_{R2c} + S_{T2c} S_{R1c}) A_{1c}}{2 S_{T2c} S_{R2c} A_{1c} - (S_{T1c} S_{R2c} + S_{T2c} S_{R1c}) A_{2c}} N_{1c}$$

$$N_c = \left\{1 + \frac{2 S_{T1c} S_{R1c} A_{2c} - (S_{T1c} S_{R2c} + S_{T2c} S_{R1c}) A_{1c}}{2 S_{T2c} S_{R2c} A_{1c} - (S_{T1c} S_{R2c} + S_{T2c} S_{R1c}) A_{2c}}\right\} N_{1c}$$

$$N_c = \frac{2 S_{T1c} S_{R1c} A_{2c} - (S_{T1c} S_{R2c} + S_{T2c} S_{R1c}) A_{1c} + 2 S_{T2c} S_{R2c} A_{1c} - (S_{T1c} S_{R2c} + S_{T2c} S_{R1c}) A_{2c}}{2 S_{T2c} S_{R2c} A_{1c} - (S_{T1c} S_{R2c} + S_{T2c} S_{R1c}) A_{2c}} N_{1c}$$

$$N_c = \frac{2 S_{T1c} S_{R1c} A_{2c} + 2 S_{T2c} S_{R2c} A_{1c} - (S_{T1c} S_{R2c} + S_{T2c} S_{R1c})(A_{1c} + A_{2c})}{2 S_{T2c} S_{R2c} A_{1c} - (S_{T1c} S_{R2c} + S_{T2c} S_{R1c}) A_{2c}} N_{1c}$$

$$N_{1c} = \frac{2 S_{T2c} S_{R2c} A_{1c} - (S_{T1c} S_{R2c} + S_{T2c} S_{R1c}) A_{2c}}{2 S_{T1c} S_{R1c} A_{2c} + 2 S_{T2c} S_{R2c} A_{1c} - (S_{T1c} S_{R2c} + S_{T2c} S_{R1c})(A_{1c} + A_{2c})} N_c$$

$$N_{2c} = \frac{2 S_{T1c} S_{R1c} A_{2c} - (S_{T1c} S_{R2c} + S_{T2c} S_{R1c}) A_{1c}}{2 S_{T1c} S_{R1c} A_{2c} + 2 S_{T2c} S_{R2c} A_{1c} - (S_{T1c} S_{R2c} + S_{T2c} S_{R1c})(A_{1c} + A_{2c})} N_c \quad \text{(Equation 51)}$$

The maximum transmission/reception sensitivity $S_c$ is obtained in the element $60c$ (the ultrasound unit $30c$) in which the number $N_{1c}$ of the first cells 9Ac and the number $N_{2c}$ of the second cells 9Bc satisfy (Equation 50) and (Equation 51).

Also, the number (the ratio) of the cells 9 is not strictly limited to the number shown in (Equation 50) or the like, and the number only needs to be within a range of ±10% from the number shown in (Equation 50) or the like according to a relationship of arrangement or the like within the element.

That is, the number $N_{1c}$ of the first cells 9Ac only needs to satisfy following (Expression 50A) with respect to the number (Z) shown in (Equation 50).

$$Z \cdot 0.9 \leq N_{1c} \leq Z \cdot 1.1 \quad \text{(Expression 50A)}$$

For example, $N_{1c} = 800$ and $N_{2c} = 200$ when $N_c = 1000$, the transmission sensitivity $S_{T1c} = 100$ Pa/V, the transmission sensitivity $S_{T2c} = 20$ Pa/V, the reception sensitivity $S_{R1c} = 300$ pV/Pa, the reception sensitivity $S_{R2c} = 900$ pV/Pa, the area $A_c = 4.2$ mm², the area $A_{1c} = 4000$ μm², and $A_{2c} = 5000$ μm².

Note that the effect is obtained when the number $N_{1c}$ of the first cells 9Ac is 720 (800×0.9) or more to 880 (800×1.1) or less as already described above.

Since the ultrasound unit $30c$ has both of the effects of the ultrasound units 30 and $30b$, the ultrasound unit $30c$ has higher transmission/reception sensitivity. The ultrasound endoscope 2c including the ultrasound unit 30c has higher transmission/reception sensitivity.

The present invention is not limited to the aforementioned embodiments or the like, and various changes, modifications, etc. can be made therein without departing from the scope of the present invention.

What is claimed is:

1. An ultrasound unit comprising:
a plurality of ultrasound transducer elements, wherein each of the plurality of ultrasound transducer elements comprises:
N ultrasound transducer cells comprising:
$N_1$ first ultrasound transducer cells, wherein each of the $N_1$ first ultrasound transducer cells comprises:
a first bottom electrode; and
a first membrane comprising a first top electrode, wherein the first bottom electrode and the first top electrode are arranged to face each other with a first cavity therebetween; and
$N_2$ (where $N_1 \neq N_2$, $N_1 + N_2 = N$) second ultrasound transducer cells, wherein each of the $N_2$ second ultrasound transducer cells comprises:
a second bottom electrode; and
a second membrane comprising a second top electrode, wherein the second bottom electrode and the second top electrode are arranged to face each other with a second cavity therebetween,
wherein the each of the $N_1$ first ultrasound transducer cells and the each of the $N_2$ second ultrasound transducer cells are configured such that the each of the $N_2$ second ultrasound transducer cells have higher reception sensitivity and lower transmission sensitivity than the each of the $N_1$ first ultrasound transducer cells,
wherein the first top electrode is electrically connected with the second top electrode, and the first bottom electrode is electrically connected with the second bottom electrode such that the N1 first ultrasound transducer cells and the N2 second ultrasound transducer cells are configured to be driven to transmit ultrasound together or to receive ultrasound together, and
wherein the $N_1$ first ultrasound transducer cells and the $N_2$ second ultrasound transducer cells have membranes having different thicknesses.

2. The ultrasound unit according to claim 1,
wherein each of the $N_1$ first ultrasound transducer cells has transmission sensitivity $S_{T1}$ and reception sensitivity $S_{R1}$,
wherein each of the $N_2$ second ultrasound transducer cells has transmission sensitivity $S_{T2}$ (where $S_{T1} > S_{T2}$) and reception sensitivity $S_{R2}$ (where $S_{R1} < S_{R2}$), and
wherein a following expression is satisfied:

$$0.9X \leq N_1 \leq 1.1X,$$

where $$X = \frac{2S_{T2}S_{R2} - S_{T1}S_{R2} - S_{T2}S_{R1}}{2(S_{T1} - S_{T2})(S_{R1} - S_{R2})} N.$$

3. The ultrasound unit according to claim 1,
wherein each of the $N_1$ first ultrasound transducer cells has an area $A_1$, and each of the $N_2$ second ultrasound transducer cells has an area $A_2$ (where $A_1 \neq A_2$).

4. The ultrasound unit according to claim 1,
wherein each of the $N_1$ first ultrasound transducer cells has transmission sensitivity $S_{T1}$, reception sensitivity $S_{R1}$, and an area $A_1$,
wherein each of the $N_2$ second ultrasound transducer cells has transmission sensitivity $S_{T2}$ (where $S_{T1} > S_{T2}$), reception sensitivity $S_{R2}$ (where $S_{R1} < S_{R2}$), and an area $A_2$ (where $A_1 \neq A_2$), and a following expression is satisfied:

$$0.9Z \leq N_1 \leq 1.1Z,$$

where $$Z = \frac{2S_{T2}S_{R2}A_1 - (S_{T1}S_{R2} + S_{T2}S_{R1})A_2}{2S_{T1}S_{R1}A_2 + 2S_{T2}S_{R2}A_1 - (S_{T1}S_{R2} + S_{T2}S_{R1})(A_1 + A_2)} N.$$

5. An ultrasound endoscope comprising:
an insertion portion comprising a distal end portion,
wherein the distal end portion comprises the ultrasound unit according to claim 1.

* * * * *